United States Patent [19]  
Wegerhoff et al.

[11] 3,954,879  
[45] May 4, 1976

[54] PROCESS FOR PRODUCING HYDROPEROXIDES

[75] Inventors: Arno Wegerhoff, Worth (Main); Dieter Frank, Elsenfeld, both of Germany

[73] Assignee: Akzona Incorporated, Asheville, N.C.

[22] Filed: Dec. 4, 1972

[21] Appl. No.: 311,542

[30] Foreign Application Priority Data  
Dec. 2, 1971 Germany............................ 2159764

[52] U.S. Cl............................................. 260/610 B
[51] Int. Cl.²...................................... C07C 179/02
[58] Field of Search..................... 260/610 B, 610 A

[56] References Cited  
UNITED STATES PATENTS

| | | | |
|---|---|---|---|
| 2,430,864 | 11/1947 | Farkas et al. | 260/610 |
| 2,619,510 | 11/1952 | Armstrong et al. | 260/610 |
| 2,715,646 | 8/1955 | Hawkins et al. | 260/10 |
| 2,724,729 | 11/1955 | Lorand | 260/610 |
| 2,776,320 | 1/1957 | Thompson | 260/610 |
| 3,092,587 | 6/1963 | Ester et al. | 252/426 |

FOREIGN PATENTS OR APPLICATIONS

| | | | |
|---|---|---|---|
| 676,722 | 8/1952 | United Kingdom | 260/610 B |

*Primary Examiner*—James O. Thomas, Jr.  
*Assistant Examiner*—W. B. Lone  
*Attorney, Agent, or Firm*—Johnston, Keil, Thompson & Shurtleff

[57] ABSTRACT

A process for producing a hydroperoxide in highly concentrated form by oxidation of its corresponding liquid hydrocarbon with oxygen or an oxygen-containing gas while simultaneously subjecting the liquid reaction mixture to a carrier gas distillation to remove unreacted hydrocarbon with the carrier gas while withdrawing a portion of the liquid reaction mixture which is enriched in the hydroperoxide.

20 Claims, No Drawings

PROCESS FOR PRODUCING HYDROPEROXIDES

It is known that secondary and tertiary alkyl-aromatic hydrocarbons such as cumene or ethylbenzene can be converted into the corresponding hydroperoxides, e.g. cumene hydroperoxide or ethylbenzene hydroperoxide, through oxidation with oxygen or an oxygen-containing gas such as air at elevated temperatures in the presence or absence of a catalyst. The reaction is briefly described for example in Fieser and Fieser, "Advanced Organic Chemistry," Reinhold Publ. Co. (1961), pages 125–128, and see also page 288. Under the reaction conditions of the known processes, the hydroperoxide product undergoes an autocatalytic decomposition to an increasing extent as the hydroperoxide concentration of the reaction mixture increases. It is therefore essential to interrupt the reaction when only about 30 to 50 percent of the hydrocarbon has been converted into the hydroperoxide. In order to prepare a highly concentrated hydroperoxide, the crude reaction mixture obtained in this known process must first be treated to remove unreacted hydrocarbon, e.g. by distillation.

One object of the present invention is to convert hydrocarbons into their corresponding hydroperoxides in such a manner as to obtain a concentrated hydroperoxide directly from the reaction mixture while also avoiding the excessive formation of undesired by-products. Another object of the invention is to provide a continuous production of the hydroperoxide in concentrated form in a single stage reaction zone. Other objects and advantages of the invention will become more apparent upon consideration of the following detailed disclosure.

It has now been found, in accordance with the invention, that an organic hydroperoxide can be produced continuously in a highly concentrated form through oxidation of its corresponding liquid hydrocarbon with oxygen or an oxygen-containing gas such as air at an elevated temperature by carrying out the steps comprising: contacting the liquid hydrocarbon with the oxygen in a reaction zone maintained at the reaction temperature to form a reaction mixture containing the hydroperoxide product together with unreacted hydrocarbon, simultaneously subjecting the reaction mixture to a rectifying carrier gas distillation for removal of an overhead fraction consisting predominately of unreacted hydrocarbon together with the carrier gas, and withdrawing a residual bottoms fraction from the reaction zone to separate that portion of the reaction mixture in which the hydroperoxide product is more highly concentrated.

In general, it is understood that a carrier gas distillation or a carrier vapor distillation refers to a distillative separation of a liquid mixture in a stream of a carrier gas or a carrier vapor wherein the more readily volatile components distil off with the carrier gas or vapor while the less volatile components remain behind as a sump. In these distillations, one can use a substance as the carrier gas or vapor which is liquid under normal conditions. That technique which is more exactly designated as a vapor carrier distillation is frequently used in industry. For example, vapor carrier distillation includes the well-known steam distillations, the "circulating out" of water with benzene, xylene or methylene chloride as the carrier vapor in the form of azeotropic mixtures, as well as other azeotropic distillations or dewatering of solvents. Substances which are gases under normal conditions, for example such as nitrogen or oxygen, can also be used as a carrier gas. However, this method of working with a gas is seldom used in industry.

In the process according to the invention, the autooxidation of the hydrocarbon takes place as a gas-liquid phase reaction simultaneously with the carrier gas distillation or rectifying separation of the reaction mixture by means of a stream of the carrier gas. In other words, both the oxidation and separation takes place continuously in a single stage. It has been found that this procedure causes a strong hydroperoxide concentration gradient to develop within the reaction mixture, and in fact such that the desired hydroperoxide accrues in higher concentration as the more difficultly volatile component in a lower layer of the reaction mixture while the upper layer of the reaction mixture consists predominantly of the more easily volatile hydrocarbon reaction component. This upper layer contains only a very slight amount of the hydroperoxide. For example, if cumene is oxidized with oxygen gas as the oxidizing agent and also as the carrier gas as described in Example 1 below at 120°C., then the hydroperoxide concentration gradient after 90 minutes of the reaction extends from about 90% by weight in the lowermost layer of the reaction zone up to about 1% by weight in the uppermost layer of the reaction zone. As a result of this concentrating effect, the hydroperoxide product can be withdrawn from the reaction zone after a relatively short retention or residence time by separating the bottom portion of the reaction mixture which is highly concentrated with the desired product. Moreover, the procedure followed according to the invention substantially reduces the formation of by-products and secondary products of the oxidation which are favored under reaction conditions at higher peroxide concentrations.

It is essential for purposes of the present invention that the reaction mixture arising in the oxidation reaction be simultaneously separated by the carrier gas distillation. Especially favorable results are achieved if the distillation proceeds more rapidly than the oxidation, i.e. if more molecules per unit volume leave or depart from the reaction and separating zone as compared to the number of hydroperoxide molecules being formed in the same unit volume. In order to obtain the best results by observing these conditions, it is desirable to observe and control the following variables: temperature, pressure, relative volatility of the hydrocarbon and hydroperoxide components being separated and the flow velocity of the carrier gas.

In principle, all of the hydrocarbon used as initial material for oxidation into the hydroperoxide can be reacted in the process according to the invention provided that this hydrocarbon is sufficiently volatile at a total pressure up to 30 atmospheres gauge and also provided that the relative volatility between the non-reacted hydrocarbon and the hydroperoxide product is sufficiently high in the noted pressure range. In carrying out the process at normal or atmospheric pressure, a hydrocarbon reactant can be considered sufficiently volatile if it exhibits a vapor pressure (partial pressure) in the range of about 40 to 750 mm.Hg. Especially favorable results are achieved with hydrocarbons if their vapor pressure lies between about 300 and 750 mm.Hg under the noted conditions. Under these circumstances, the distillative separation takes place rapidly and can be carried out moreover at relatively slower speeds of the carrier gas stream. As a rule, the hydroperoxide also possesses a much lower vapor pressure than the corresponding hydrocarbon from which it is obtained, so that the necessary difference in relative volatility is sufficiently high. Examples of hydrocarbons which fulfill these conditions and can therefore be used in the process of the invention include aromatic hydrocarbons such as, for example, cumene, p-diisopropylbenzene, m-diisopropylbenzene and sec.-butylbenzene, or aliphatic hydrocarbons such as, for example, isobutane and n-decane, and also alicyclic hydrocarbons such as cyclooctane and cyclohexane. Especially preferred hydrocarbons for use in the oxidation process of the invention are cumene, m-diisopropylbenzene, ethylbenzene, n-decane and cyclooctane. On the other hand, the present invention is applicable to any hydrocarbon which can be suitably transformed into its hydroperoxide even though for practical purposes the present invention may be limited to alkanes, alkylbenzenes or cycloalkanes of about 4 to 20 carbon atoms, preferably 8 to 16 carbon atoms.

The process according to the invention is preferably carried out at normal or atmospheric pressure.

The temperature influences not only the speed of the oxidation reaction but also the basic result intended by the invention because of the dependency of the partial pressure of the components on the temperature. The temperatures used in the process of the invention are therefore regulated to conform with the individual hydrocarbon. In general, the temperature selected depends both upon the reactivity and also the volatility of the hydrocarbon being used in the reaction. On the one hand, the reactant temperature must be sufficiently high to guarantee a satisfactory reaction, but on the other hand, the temperature must not be so high that an oxidation occurs more rapidly or more extensively than the simultaneously conducted carrier gas distillation. Within a given temperature range, it is advantageous to choose the highest possible temperature because a high conversion is then achieved and simultaneously the more difficultly volatile hydroperoxide is rapidly separated by distillation due to the increasing volatility of the unreacted hydrocarbon with increasing temperature. For example, the temperature range is relatively broad when using cumene as the initial reactant, i.e. a range at normal pressure of from about 80° to 140°C. Preferably, the auto-oxidation of cumene takes place at 110° to 130°C. at normal or atmospheric pressure.

With other hydrocarbon reactants, the temperature range is generally narrower, but all of the preferred hydrocarbon reactants can generally be reacted within an overall range of about 80° to 175°C. at normal pressure. If one works above or below atmospheric pressure, the temperatures must be adjusted accordingly.

By way of further example, the temperature range when working with ethylbenzene at normal pressure can range from about 100° to 135°C. With an increase in the total pressure up to 5 atmospheres gauge, the auto-oxidation of ethylbenzene can be carried out at higher temperatures, for example at 135°–150°C. As examples of the preferred class of hydrocarbon reactants, the following temperature ranges at normal pressure can be mentioned: ethylbenzene, 100°–135°C. and preferably 125°–135°C.; m-diisopropylbenzene, 100°–140°C. and preferably 110°–130°C.; n-decane, 110°–172°C. and preferably 140°–170°C.; and cyclooctane, 110°–146°C. and preferably 120°–140°C. When working with other hydrocarbons, the most suitable temperature range for carrying out the process of the invention can be readily determined in a simple manner by preliminary experiments. In all cases, one observes the general rule that the distillative separation should occur more rapidly than the oxidation. Otherwise, the reaction temperature is preferably maintained as high as possible.

As an inert carrier gas, it is possible to use nitrogen, steam or nitrogen and steam mixtures. One can also use other inert gases but this usually is not practical from an economical viewpoint. Also, one can completely avoid the use of the inert carrier gases if the oxygen or oxygen-containing gas such as air is used in excess over that required for oxidation of the hydrocarbon. In this case, the oxidation gas also assumes the role of the carrier gas. As the carrier gas, it is thus preferable to employ oxygen, air, oxygen and steam mixtures or air and steam mixtures. In the use of steam or steam-containing carrier gases, it is necessary to separate the water from the hydrocarbon before returning the hydrocarbon to the reaction vessel, i.e. after the water has been separated together with the hydrocarbon from the off-gas of the reaction by condensation. This separation of the water from the condensed hydrocarbon can be easily carried out, for example by use of a conventional water separator which is preferably arranged at the upper outlet of the reaction vessel.

Even in the use of a water-free carrier gas, it can be advantageous to subject the off-gas to a condensation of the hydrocarbon followed by a separation of water, for example in those cases such as the oxidation of paraffinic hydrocarbons wherein water and sometimes highly volatile water-soluble carboxylic acids arise as by-products. Without insertion of a water separator, the water is recycled together with the non-reacted hydrocarbon into the reaction vessel, and after a long period of operation, the water finally becomes concentrated in the upper reaction zone, thereby leading to disturbances of the continuous oxidation.

The speed at which the oxygen or oxygen-containing gas is introduced into the reaction zone, as well as that of any inert carrier gas, conforms essentially to the temperature or to the vapor pressure of the individual hydrocarbon at the appropriate temperature of the reactant. The geometric relationships within the reactor are also of influence. In the process according to the invention, the lowest velocities of the carrier gas stream are observed when the reaction temperature lies at or directly under the boiling point of the hydrocarbon reactant.

The reaction is preferably carried out in a reaction vessel or reaction zone filled with a fibrous filler. It is also feasible to employ other similar compact filler bodies. The process of the invention is then preferably carried out in such a manner that the hydrocarbon is introduced in liquid form into the upper portion of the reactor, the oxygen or oxygen-containing gas as well as any inert carrier gas being introduced into the lower portion of the reactor. The unreacted gaseous hydrocarbon entrained with the carrier gas from the top of the reactor is condensed and preferably separated from water and any volatile water-soluble carboxylic acids, and this unreacted hydrocarbon can then be recycled to the reactor. A highly concentrated hydroperoxide mixture is withdrawn from the lower portion of the reactor in a continuous manner.

While it is possible to introduce conventional inert filler bodies such as Raschig rings, Berl saddles or wire coils, the basic results are not so good as when using a fibrous filler. As in any normal rectification, these fibers provide for a substantial increase in surface area between the gas and liquid phases, thereby yielding an intensive interchange of materials. As distinguished from a rectification, however, the velocity of the rising gas or vapor streams in this liquid phase auto-oxidation coupled with a carrier gas distillation are essentially greater because one must take into consideration not only the energy supplied by heating and the exothermically running oxidation but also the kinetic energy of the carrier gas being conducted through the reactor.

The reaction vessel required for carrying out the process of the invention can be of a simple construction. It must be capable of being heated, for example by means of a jacketed external heating means which may be supplemented by internal indirect heat exchange means. Of course, the vessel must also be provided with the necessary inlet and outlet conduits for the reactant components and products as well as with a cooling system for the recovery of the unreacted hydrocarbon. By way of example, suitable reactant vessels include reaction tubes, spherical condensers and plate-type columns.

As the preferred fibrous filler, one can use either catalytic or non-catalytic materials. Particularly good results have been achieved by using fibers composed of metal complex compounds of polyacyloxalamidrazones. These catalytic fibers are composed of the metal in complex combination (e.g. as in enols and similar complex compounds) with a polymer having recurring units of the tautomeric formulae

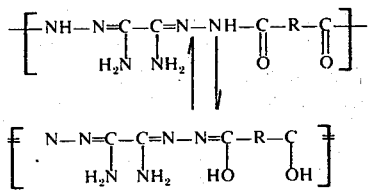

in which R is preferably a divalent hydrocarbon radical of about 2 to 20 carbon atoms, preferably about 4 to 12 carbon atoms, but may also be any straight or branched chain aliphatic radical of preferably 2–12 carbon atoms, or else a cycloaliphatic radical of preferably 6 to 8 carbon atoms, an araliphatic or aromatic radical of preferably 6 to 14 carbon atoms or even a heterocyclic radical in which the hydrocarbon chain is interrupted, e.g. by oxygen or nitrogen. These polymers have been described in detail in Belgian Pat. Nos. 705,592 and 720,790.

The polyacyloxalamidrazones are obtained by reaction of at least one dicarboxylic acid of the formula

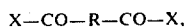

wherein R has the same meaning as given above and X is chlorine or bromine, with oxalic acid bisamidrazone. The metal-complex compounds of the polymer can be prepared according to the process disclosed in Belgian Pat. No. 748,357, i.e. by reaction of the polyacyloxalamidrazone with a solution of the metal compound. The metal can be introduced before or preferably after spinning into filaments or fibers. Suitable examples of such fibers are those obtained from the compounds of polyterephthaloyl-, polyisophthaloyl-, polyfumaroyl-, poly-2,6-naphthalenoyl-, polyadipoyl-, polysebacinoyl- or poly-2,6-pyridinoyl-oxalic acid bisamidrazone with one or more metals selected from the group consisting of copper, cobalt, nickel, cerium, lead and calcium. Especially preferred are the fibers composed of the metal-complex compounds of polyterephthaloyl- and polyfumaroyl-oxalamidrazone, particularly when using at least one metal from the group consisting of copper, cobalt and nickel. These fibers can be produced, for example, according to the process set forth in Belgian Pat. No. 748,358.

As non-catalytic fibrous fillers, one can use glass fibers, filamentary glass coils, wire mesh saddle bodies or the like. Any kind of packing or filler which provides a large interchange surface and/or increases the retention time per unit length has at least some beneficial effect. In principle, it is desirable to fill or pack the reaction vessel with fibers or filaments, for example, so tightly that a back-mixing of the carrier gas distilled or entrained reaction components through uncontrolled turbulence can no longer take place. On the other hand, the reaction vessel or reaction zone cannot be so tightly filled or packed that the stream of carrier gas is able to convey the entrained portions of the reaction mixture into the attached condenser or cooling system.

With many hydrocarbons such as cumene, the conversion to the hydroperoxide is autocatalytic so that it is sometimes desirable to employ only a catalyst initiator, i.e. a very small amount of a free radical initiator including the well-known peroxide initiators. Other conventional measures can also be observed in the oxidation reaction of the invention without loss of the essential improvement gained in combining the auto-oxidation reaction with the carrier gas distillation.

In order to carry out the reaction according to the invention, there is preferably employed a bulbular reaction tube (spherical condenser type) as the reaction vessel. By reason of its special geometric configuration, this type of reactor leads to a periodic variation between lower and higher gas velocities whereby turbulence arises at narrow points or cross-sections in known manner. This in turn causes a partial reversal of the stream direction and thereby works against any tendency toward damming or obstruction. At the same time, this flow reversal is too slight to have any overall effect on the concentration gradient of the hydroperoxide over the height of the reactor. When using a cylindrical reaction vessel, the fibers are preferably arranged in several separate superimposed layers one over the other. For example, such fibrous layers can be defined and supported by sieve plates or the like. Thus, one can simply use a sieve-plate column of conventional design wherein the plates are covered with the fibrous filler material.

In the process of the invention, there is collected not only the hydroperoxide as the main product which is more highly concentrated in the reaction mixture withdrawn from the lower end of the reaction vessel, but also those by-products which are also only difficultly volatile and therefore drawn off together with the desired product, e.g. such by-products in the auto-oxidation of cumene as both acetophenone and also dimethylphenylcarbinol. It is a definite advantage of the invention that such by-products accumulate in much smaller amounts in comparison to previously known processes.

The invention is further explained by means of the following working examples which only illustrate the invention.

EXAMPLE 1

A 50 cm. long bulbular reaction vessel was employed with a capacity of 216 ml. in which 11 grams of glass fibers were uniformly distributed. The vessel was connected at its upper end to a feed line for the hydrocarbon reactant and with a reflux condenser. A gas inlet line as well as a discharge conduit for the reaction mixture were attached at the bottom end of the reaction vessel.

This apparatus as a spherical-type or bulbular reactor was filled with 70 grams of cumene and then heated to 120°C. Through the gas inlet line at the bottom of the reactor there was introduced 50 N liters/hour of oxygen. (N=S.T.P., i.e. the amount of gas being measured with reference to standard temperature and pressure conditions as is conventional.)

First after one hour and then at intervals of one-half hour, there was taken from the base of the reaction tube only so much of the reaction mixture, i.e. the autooxidate, that the cumene hydroperoxide content of the removed product amounted to 80–90% by weight. The control of the hydroperoxide concentration took place by measurement of the refractive index with the aid of a calibration curve. The removed volumetric amounts of the product were replaced by dropwise feeding of fresh cumene at the top of the reactor.

After 7 hours operation, there was obtained a total amount of 21.7 ml. which corresponds to 22.5 grams of the bottoms reaction mixture having the following composition:

| Compound | % by wt. | Mol % |
| --- | --- | --- |
| Cumene hydroperoxide | 85.1 | 81.9 |
| Unreacted cumene | 12.6 | 15.4 |
| Dimethylphenylcarbinol | 0.5 | 0.5 |
| Acetophenone | 1.8 | 2.2 |
| Totals | 100.0 | 100.0 |

From these values, the yield of cumene hydroperoxide can be calculated as 81.9 percent of theory while the selectivity is 96.8 percent.

EXAMPLE 2

The apparatus as described in Example 1 was filled with 70 grams of m-diisopropylbenzene for oxidation into the corresponding hydroperoxides. In this case, however, a water separator was inserted between the reaction tube or vessel and the reflux condenser in order to continuously separate water when using steam as the carrier gas and condensing this steam in the reflux condenser together with unreacted hydrocarbon. This permitted a return of this unreacted hydrocarbon without causing a build-up of water in the reaction vessel. The reaction temperature was maintained at 125°C. The oxidizing agent and carrier gas was a mixture of 30 N liters/hour oxygen and 2 mols/hour of steam.

After 7 hours of operation under these conditions, with removal of the reaction mixture and fresh hydrocarbon feed at the top as in Example 1, there was obtained a bottoms product in an amount of 54.4 grams having the following composition (m-DIPB = m-diisopropylbenzene).

| Compound | % by wt. |
| --- | --- |
| Monohydroperoxide of m-DIPB | 71 |
| Dihydroperoxide of m-DIPB | 15 |
| Unreacted m-DIPB | 10 |
| By-products (approx.) | 4 |
| Total | 100 |

EXAMPLE 3

In the following tests, there is described an oxidation of a $C_{10}$-benzine (gasoline) fraction having a boiling point of 170°–175°C. and a content of n-decane calculated as 85–90% by weight. The apparatus and procedure corresponded to that used in Example 1 except as otherwise noted.

70 grams of the $C_{10}$-hydrocarbon (benzine fraction) was oxidized with 25 N liters/hour of air at 160°C. Over a time period of seven hours, there was withdrawn altogether 31.9 grams of autooxidate as a bottoms product while replacing the withdrawn amounts by volume with the dropwise addition of a corresponding amount by volume of the $C_{10}$-hydrocarbon. The product contained 28.8% by weight of the corresponding $C_{10}$-hydroperoxides, calculated as decane monohydroperoxide, plus 56.5% by weight of non-reacted hydrocarbon as well as 14.7% by weight of by-products (primarily the corresponding ketones, alcohols, carboxylic acids and esters).

Comparison

Under the same general reaction conditions given above, 70 grams of the $C_{10}$-hydrocarbon were oxidized without concentration of the hydroperoxide, i.e. without using the carrier gas distillation in the same stage with the oxidation reaction. Also, the reaction vessel contained no fibrous filler. During the reaction, no part of the autooxidate was removed and no fresh hydrocarbon was added. After 7 hours, the hydroperoxide content of the reaction mixture amounted to only 2.9% by weight while the content of unreacted hydrocarbon was then 70.8% by weight and the content of by-products was 26.3% by weight.

EXAMPLE 4

For the autooxidation of ethylbenzene, there was used as the reaction vessel a 1.3 liter capacity tube which was 94.5 cm. long and heated from the outside. Glass fibers were arranged in layers in the interior of the tube such that the upper portion of the tube was less densely and more loosely filled than the lower portion. There was oxidized 500 grams of ethylbenzene at 135°C. with 50 N liters/hour of air. The withdrawal of the autooxidate as a bottoms product first took place after one hour and then at quarter-hour intervals with the withdrawn portions by volume being replaced by dropwise addition of a corresponding amount of ethylbenzene at the top of reaction zone.

After 7 hours, the thus obtained autooxidate product amounted altogether to 182.2 grams having the following composition:

| Compound | % by wt. | Mol % |
| --- | --- | --- |
| Ethylbenzene hydroperoxide | 13.9 | 11.05 |
| Acetophenone | 0.80 | 0.73 |
| α-phenylethanol | 0.46 | 0.42 |
| Unreacted ethylbenzene | 84.8 | 87.8 |
| Undetermined | 0.04 | — |

| Compound | % by wt. | Mol % |
|---|---|---|
| Totals | 100.00 | 100.00 |

The selectivity of this ethylbenzene autooxidation with reference to hydroperoxide formation was calculated from these values as amounting to 90.6 percent.

The acid content of the ethylbenzene hydroperoxide produced according to Example 4 amounted to 1.8 milliequivalents/kg. or, calculated on the basis of benzoic acid, about 0.022% by weight. This is much less acid than that obtained in the corresponding known process.

For any industrial use of ethylbenzene hydroperoxide, e.g. as an epoxidizing agent for olefins, it is very important that the carboxylic acid content be as small as possible.

EXAMPLE 5

In this example there is set forth the catalytic autooxidation of cyclooctane through the use of copper-polyterephthaloyloxalamidrazone fibers as the catalyst. The copper content of the catalyst fibers was 11.3% by weight. As described generally in Example 4, 400 grams of cyclooctane were oxidized with 100 N liters/hour of air at 120°C. in the reaction tube filled with the catalyst fibers. Otherwise, the procedure corresponded to Example 4.

After 7 hours, there was obtained a total amount of 84.2 grams of the autooxidate as the bottoms provided with the following composition:

| Compound | % by wt. | Mol % |
|---|---|---|
| Cyclooctane hydroperoxide | 32.7 | 27.9 |
| Cyclooctanone | 7.3 | 7.1 |
| Cyclooctanol | 6.7 | 6.4 |
| Unreacted cyclooctane | 53.3 | 58.6 |
| Totals | 100.0 | 100.0 |

From these values, the selectivity of the cyclooctane oxidation with reference to the desired formation of the hydroperoxide amounted to 67.4 percent.

EXAMPLE 6

The reaction vessel described in Example 1 served as the bulbular reaction tube in which 4.0 grams of glass fibers were uniformly distributed. 70 grams of n-decene-(1) were oxidized at 130°C. with 50 N liters/hour of air. The autooxidate as a bottoms product was first recovered after 2 hours of reaction with air as described in Example 1. Thereafter, the product was withdrawn at quarter-hour intervals, fresh hydrocarbon being introduced dropwise each time to replace the parts by volume of withdrawn reaction mixture.

After 3½ hours there was obtained a total of 30.7 grams of reaction product having the following composition:

| | |
|---|---|
| Hydroperoxide (calculated as decene-monohydroperoxide) | 10.1% by wt. |
| By-products (primarily 1,2-decane epoxide) | 9.7% by wt. |
| Unreacted n-decene-(1) | 80.2% by wt. |
| Total | 100.0 |

Comparison

There was oxidized 70 grams of n-decene-(1) in the same reaction tube under the same conditions of this example, except without any fibrous filler in the reaction tube. During the oxidation, there resulted no corresponding enrichment of the difficulty volatile reaction product because no carrier gas distillation took place. After 3½ hours, the entire reaction mixture was drawn off and analyzed as follows to show a substantially increased proportion of by-products:

| | |
|---|---|
| Hydroperoxide | 7.1% by wt. |
| By-products | 18.0% by wt. |
| Unreacted n-decene-(1) | 74.9% by wt. |
| Total | 100.0 |

The process of the invention is thus broadly applicable to both saturated and unsaturated hydrocarbons, i.e. including both alkanes and alkenes as well as cumene and similar alkylaromatic hydrocarbons or cyclohexane, cyclooctane and similar cycloalkanes. Although some products are obtained in relatively low yields, depending upon the initial reactant, the results are still far better than can be achieved in previous batch or semi-continuous processes. The term "continuous" is employed herein to include semi-continuous operation, i.e. where product is removed at regular intervals and then only gradually replacing the volume of reaction mixture withdrawn with a dropwise addition of fresh hydrocarbon reactant.

In those instances where water and/or carboxylic acids tend to collect in the overhead product of unreacted hydrocarbon, it is preferable to include the step of water separation after condensation of the hydrocarbon vapor and before the condensed hydrocarbon is returned to the reaction zone.

By simultaneously oxidizing the hydrocarbon into its hydroperoxide and subjecting the reaction mixture to a carrier gas distillation, there are considerably fewer side reactions or loss of valuable hydroperoxide products. Moreover, by obtaining the product in a relatively highly concentrated form, one can be more certain of achieving a highly useful hydroperoxide product. In some instances, this product requires practically no after-treatment. Even where the theoretical yield is low, however, the selectivity is comparatively high and the amount of by-products is exceptionally low.

The invention is hereby claimed as follows:

1. In a continuous process for the production of an organic mono- or di-hydroperoxide by oxidation of its corresponding hydrocarbon in the liquid state with oxygen or an oxygen-containing gas at an elevated temperature of approximately 80°–175°C with reference to normal pressure, the improvement which comprises:

contacting the liquid hydrocarbon with the oxygen in a reaction zone maintained at the reaction temperature to form a reaction mixture containing the hydroperoxide product together with unreacted hydrocarbon;

simultaneously subjecting the reaction mixture to a rectifying carrier gas distillation in the same zone as the reaction zone for removal of an overhead fraction consisting predominately of unreacted hydrocarbon together with the carrier gas; and withdrawing a residual bottoms fraction from the reaction zone to separate that portion of the reaction mixture in which the hydroperoxide product is more highly concentrated.

2. A process as claimed in claim 1 wherein said hydrocarbon is selected from the group consisting of cumene, m-diisopropylbenzene, ethylbenzene, n-decane and cyclooctane.

3. A process as claimed in claim 1 wherein the oxidation is carried out at atmospheric pressure.

4. A process as claimed in claim 1 wherein the carrier gas is at least one gas selected from the group consisting of nitrogen, steam, oxygen or air.

5. A process as claimed in claim 1 wherein the hydrocarbon is cumene and the oxidation is carried out at a reaction temperature of about 80°C. to 140°C.

6. A process as claimed in claim 5 wherein the reaction temperature is about 100°C. to 130°C.

7. A process as claimed in claim 1 wherein the hydrocarbon is m-diisopropylbenzene and the oxidation is carried out at a reaction temperature of about 100°C. to 140°C.

8. A process as claimed in claim 7 wherein the reaction temperature is about 110°C. to 130°C.

9. A process as claimed in claim 1 wherein the hydrocarbon is ethylbenzene and the oxidation is carried out at a temperature of about 100°C. to 135°C.

10. A process as claimed in claim 9 wherein the reaction temperature is about 125°C. to 135°C.

11. A process as claimed in claim 1 wherein the hydrocarbon is n-decane and the oxidation is carried out at a temperature of about 110°C. to 172°C.

12. A process as claimed in claim 11 wherein the reaction temperature is about 140°C. to 170°C.

13. A process as claimed in claim 1 wherein the hydrocarbon is cyclooctane and the oxidation is carried out at a temperature of about 110°C. to 146°C.

14. A process as claimed in claim 13 wherein the reaction temperature is about 120°C. to 140°C.

15. A process as claimed in claim 1 wherein the oxidation is carried out in a reaction zone packed with a fibrous filler.

16. A process as claimed in claim 1 wherein the hydrocarbon is introduced continuously in liquid form at the upper end of a vessel forming the reaction zone, the oxygen or oxygen-containing gas is continuously introduced together with any inert carrier gas at the lower end of said vessel forming the reaction zone, unreacted hydrocarbon is continuously withdrawn in gaseous form at the upper end of the reaction zone, condensed and returned to said reaction zone, and a concentrated hydroperoxide is continuously withdrawn at the lower end of said reaction zone.

17. A process as claimed in claim 16 wherein the oxidation is carried out at a temperature of about 80°C. to 175°C.

18. A process as claimed in claim 16 wherein the carrier gas distillation proceeds at a rate sufficient to remove more molecules of unreacted hydrocarbon per unit volume in the reaction zone than the number of molecules of hydroperoxide being formed in the same unit volume.

19. A process as claimed in claim 18 wherein the oxidation is carried out at atmospheric pressure and a temperature of about 80°C. to 175°C.

20. A process as claimed in claim 1 wherein the hydrocarbon is selected from the group consisting of alkanes, alkylbenzenes and cycloalkanes of about 4 to 20 carbon atoms, the carrier gas is selected from the group consisting of nitrogen, steam, oxygen, air or mixtures thereof, the reaction temperature is about 80°C. to 175°C. with reference to normal pressure and the reaction is carried out at a pressure up to about 30 atmospheres gauge.

* * * * *